US005772993A

United States Patent [19]

Chung et al.

[11] Patent Number: 5,772,993
[45] Date of Patent: Jun. 30, 1998

[54] OSTEOCALCIN PROMOTER-BASED TOXIC GENE THERAPY FOR THE TREATMENT OF CALCIFIED TUMORS AND TISSUES

[75] Inventors: Leland W. K. Chung, Lovingston; Chinghai Kao, Charlottesville; Robert A. Sikes, Charlottesville; Song-Chu Ko, Charlottesville, all of Va.; Jun Cheon, Sol, Rep. of Korea

[73] Assignee: The University of Virginia Patent Foundation, Charlottesville, Va.

[21] Appl. No.: 785,088

[22] Filed: Jan. 21, 1997

[51] Int. Cl.[6] .......................... A61K 48/00; A01N 63/00; C12P 21/04; C12N 15/00

[52] U.S. Cl. ...................... 424/93.6; 514/44; 435/320.1; 435/71.2; 424/9.2

[58] Field of Search ..................................... 424/9.2, 93.6; 514/44; 435/320.1, 71.2

[56] References Cited

PUBLICATIONS

Su et al Human Gene Therapy (1996) Mar. 1 7(4) 463–70.
Henderson et al WO 9701358 Jan. 16, 1997.
Ko et al Cancer Res Oct. 15, 1996, 56(20) pp. 4614–4619.

*Primary Examiner*—Lila Feisee
*Assistant Examiner*—Geetha P. Bansal
*Attorney, Agent, or Firm*—Oblon, Spivak, McClelland, Maier & Neustadt, P.C.

[57] ABSTRACT

A recombinant adenovirus Ad-OC-TK was constructed, with cell specific gene expression, which contains osteocalcin (OC) promoter that drives the expression of herpes simplex virus thymidine kinase (TK); the addition of acyclovir (ACV), a pro-drug for the inhibition of cell proliferation, to Ad-OC-TK resulted in the induction of osteoblast-specific cell death in vitro. The Ad-OC-TK virus plus ACV treatment is highly selective in blocking the growth of both murine and human osteosarcoma cell lines in vitro and murine osteosarcoma in vivo.

6 Claims, 13 Drawing Sheets

OSTEOCALCIN PROMOTER-BASED TOXIC GENE THERAPY FOR THE TREATMENT OF CALCIFIED TUMORS AND TISSUES

BACKGROUND OF THE INVENTION

1. Field of the Invention

The present invention is directed to a novel therapeutic agent for curing a tumor with calcification potential such as localized osteosarcoma, breast and prostate cancers, melanoma and brain tumors and their osseous and lung metastases.

2. Description of the Related Art

Osteosarcoma, a bone cancer occurring primarily in teenagers and young adults, affects approximately 2100 individuals yearly in the United States (Boring, C. C., Squires, T. S., Tong, T., and Montgomery. S. Cancer statistics, 1994, CA Cancer J. Clin., 44; 7–26, 1994). This malignancy accounts for as many as 5% of all childhood malignancies and 60% of all malignant childhood bone tumors (Hudson, M., Jaffe, M. R., and Jaffe, N. Pediatric osteosarcoma: therapeutic strategies, results, and prognostic actors derived from a 10 10-year experience. J. Clin. Oncol., 8: 1988–1997, 1990). Despite radical surgical resection of the primary tumor and aggressive adjuvant chemotherapy, the overall 2-year metastasis-free survival rate approaches only 66%. More than 30% of patients with this disease develop lung metastasis within the first year (Link, M. P., Goorin, A. M., Mixer, A. W., Link, M. P., Goorin, A. M., Miser, A. W., Green, A. A., Pratt C. H., Belasco, J. B., Pritchard, J., Malpas, J. S., Baker, A. R., Kirkpatrick, J. A., Ayala, A. O., Schuster, J. J., Abelson, H. T., Simone, J. V., and Vietti, T. J. The effect of adjuvant chemotherapy on relapse-free survival in patients with osteosarcoma of the extremity. N. Engl. J. Med, 314: 1600–1602, 1991. Goorin, A. M., Perez-Atayde, A., Gebbhardt, M., et al. Weekly high-dose methotrexate and doxorubicin for osteosarcoma: the Dunn-Farber Cancer Institute/The Children's Hospital-Study III. J. Clin. Oncol., 5: 1178–1184, 1987). The survival rate among those affected with osteosarcoma has not changed significantly over the past 10 years, despite changes in adjuvant chemotherapy, Kane, M. J. Chemotherapy of advanced soft tissue and osteosarcoma. Semin. Oncol., 16:297–304, 1989.

The concept of delivery and expression of therapeutic toxic genes to tumor cells through the use of tissue-specific promoters has been well recognized. This approach could decrease the toxic effect of therapeutic genes on neighboring normal cells when virus-mediated gene delivery results in the infection of the normal cells. Examples include the uses of the albumin or a-fetoprotein promoter to target hepatoma cells (Kuriyama, S., Yoshikawa, M., Ishizaka, S., Taujli, T., Ikenaka, K., Kagawa, T., Morita, N., and Mikoshiba, K. A. potential approach for gene therapy targeting hepatoma using a liver-specific promoter on a retroviral vector, Cell Struct. Punct., 16: 503–510, 1991), the bone morphogenic protein promoter for brain to target glioma cells (Shimizu, K. Selective gene therapy of malignant glioma using brain-specific promoters; its efficacy and basic investigation, Nippon Rinsbo, 52: 3053–3058, 1994), the tyrosinase promoter to kill melanoma cells (Vile, R. G., Nelson, J. A., Castleden, S., Chong, H., and Hart, I. R. Systemic gene therapy of murine melanoma using tissue specific expression of the HSVtk gene involves an immune component. Cancer Res., 54:6228–6234, 1994), and the carcinoembryonic antigen promoter for gastric carcinoma cells (Tanaka, T., Kanai. F., Okabe, S., Yoshida, Y., Wakimoto, H., Hamada, H., Shiratori, Y., Lan, K-H., Ishitobi, M., and Omata, M. Adenovirus-mediated prodrug gene therapy for carcinoembryonic antigen-producing human gastric carcinoma cells in vitro. Cancer Res., 46: 1341–1345, 1996). To date, the best studied therapeutic gene is herpes simplex virus TK gene. Herpes simplex virus-TK converts the pro-drug ACV to a phosphorylated form that is cytotoxic to dividing cells (Moolten, F. L., Tumor chemosensitivity conferred by inserted herpes thymidine kinase genes; paradigm for a prospective cancer control strategy. Cancer Res., 46:5276–5281, 1986). Critical to successful results is the "bystander" effect, which confers cytotoxicity on neighboring nontransduced cells; effective tumor cell kill can be achieved without the delivery to and expression of suicide genes in every tumor cell in vivo. This approach has been demonstrated recently to be efficacious in causing regression of many solid tumors, including metastatic colon carcinoma in the rat liver, (Chen, S. II., Chen, X. H. L., Wang, Y., Kosal, K. E., Finegold, J. J., Rich, S. S., and Woo, S. L. C., Combination gene therapy for liver metastasis of colon carcinoma in vivo. Proc. Natl. Acad. Sci. USA. 92:2577–2581, 1995), gastric carcinoma, (Tanaka, T., Kanai. F., Okabe, S., Yoshida, Y., Wakimoto, H., Hamada, H., Shiratori, Y., Lan, K-H., Ishitobi, M., and Omata, M. Adenovirus-mediated prodrug gene therapy for carcinoembryonic antigen-producing human gastric carcinoma cells in vitro. Cancer Res., 46: 1341–1345, 1996), and malignant mesothelioma (Smythe, W. R., Hwang, B. S., Elshami, A. A., amin, K. M., Eck, S., Davidson, B. L., Wilson, J. M., Kaiser, L. R., and Albelda, S. M. Treatment of experimental human mesothelioma using adenovirus transfer of the herpes simplex thymidine kinase gene. Ann. Surg., 222:78–86, 1995).

Osteocalcin (OC), a noncollagenous Gla protein produced specifically in osteoblasts, is synthesized, secreted, and deposited at the time of bone mineralization (Price, P.A. Vitamin-K dependent formation of bone GLA protein (onteocalcin) and its function. Vitam. Horm., 42:65–108, 1985). A recent study showed that immunohistochemical staining of OC as positive in primary osteoblastic osteosarcoma and chondroblastic osteosarcoma specimens as well as in five of seven fibroblastic osteosarcomas (Park, Y. K., Yung, M. H., Kim, Y. W., and Park, H. R. Ostocalcin expression in primary bone tumors: in situ hybrodization and immunohistochemical study. J. Korean Med. Sci., 10:268–27, 1995). In addition, OC activity was detected in a wide spectrum of human tumors. This is consistent with the clinical observations that many human tumors exhibited calcification characteristics both in the primary and at distant metastases.

Because of the poor response rate of previously treated patients with relapsed osteosarcoma to second-line chemotherapy and the fact that many human solid tumors failed to respond to conventional chemotherapy and radiation therapy, it is important to develop new therapeutic approaches that can be applied either separately or in conjunction with current treatment modalities.

SUMMARY OF THE INVENTION

The present invention relates to a novel therapeutic gene comprising a recombinant adenovirus (Ad), which contains an osteocalcin (OC) promoter that drives the expression of herpes simplex virus thymidine kinase (TK), and which is represented by Ad-OC-TK, in a broad spectrum of human tumors that exhibit ability to calcify either in the primary or at metastatic sites. We noted that not only tumors but also non-tumor cells, as long as they have the ability to calcify, do express high OC-TK.

Further, the present invention provides a method of treating a prototype of tumor, osteosarcoma, by intravenous, intratumoral or isolated regional. perfusion of organs injection with the recombinant adenovirus, Ad-OC-TK. In addition, applicants have provided data to show that Ad-OC-TK eradicate the growth of localized prostate cancer and its osseous metastasis as well as the growth of brain tumor cells in vitro.

The present invention also provides a method of treating osteosarcoma by the above routes of recombinant adenovirus Ad-OC-TK administration in combination with acyclovir (ACV). Ad-OC-TK virus plus ACV treatment is highly selective in blocking the growth of both murine and human osteosarcoma cell lines in vitro, murine osteosarcoma in vivo, human brain tumor cells in vitro, prostate carcinoma cell growth both in vitro and in vivo as localized and as osseous metastatic deposit.

In addition the present invention provides a method for curing osseous metastatic tumors such as melanoma, breast cancer and prostate cancer, the treatment of tumors (e.g. osteosarcoma and prostate cancer) that metastasized to the lung, and the effect in inhibiting human brain tumor cell growth in vitro.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 9 shows that human bone tissues stained positively by osteocalcin antibody.

FIG. 10 shows that human colon cancer failed to stain by osteocalcin antibody.

FIG. 11 shows positive immunohistochemical staining oosteocalcin expression by human meningioma.

FIG. 12 shows positive immunohistochemical staining of lung bronchial alveolar carcinoma.

FIG. 13 shows positive immunohistochemical staining of papillary thyroid carcinoma.

FIG. 14 shows positive immunohistochemical staining of malignant mesothelioma.

FIG. 15 shows positive immunohistochemical staining of papillary ovarian carcinoma lung metastasis.

FIG. 16 shoes osteocalcin TK expression in various human brain tumor cell lines. Note: In comparison to rat osteosarcoma (assigned as 100%), an array of human brain tumor cell lines, including SK-N-SH (a human neuroblastoma cell line), A172 (a human glioblastoma cell line), H4 (a human neuroglioma cell line), HS 683 (a human glioma cell line), CH157MN (a human meningioma cell line), and HOG (a human oligodendroglioma cell line) all expressed high levels of osteocalcin TK activity; however, TLB-G (a normal human glial cell line), TC620 (a normal human oligodendrocyte cell line), WH (a human bladder transitional cell carcinoma ceL1 line), and NIH 3T3 (a mouse fibroblast cell line) expressed low levels of osteocalcin TK activity.

Figure 1:
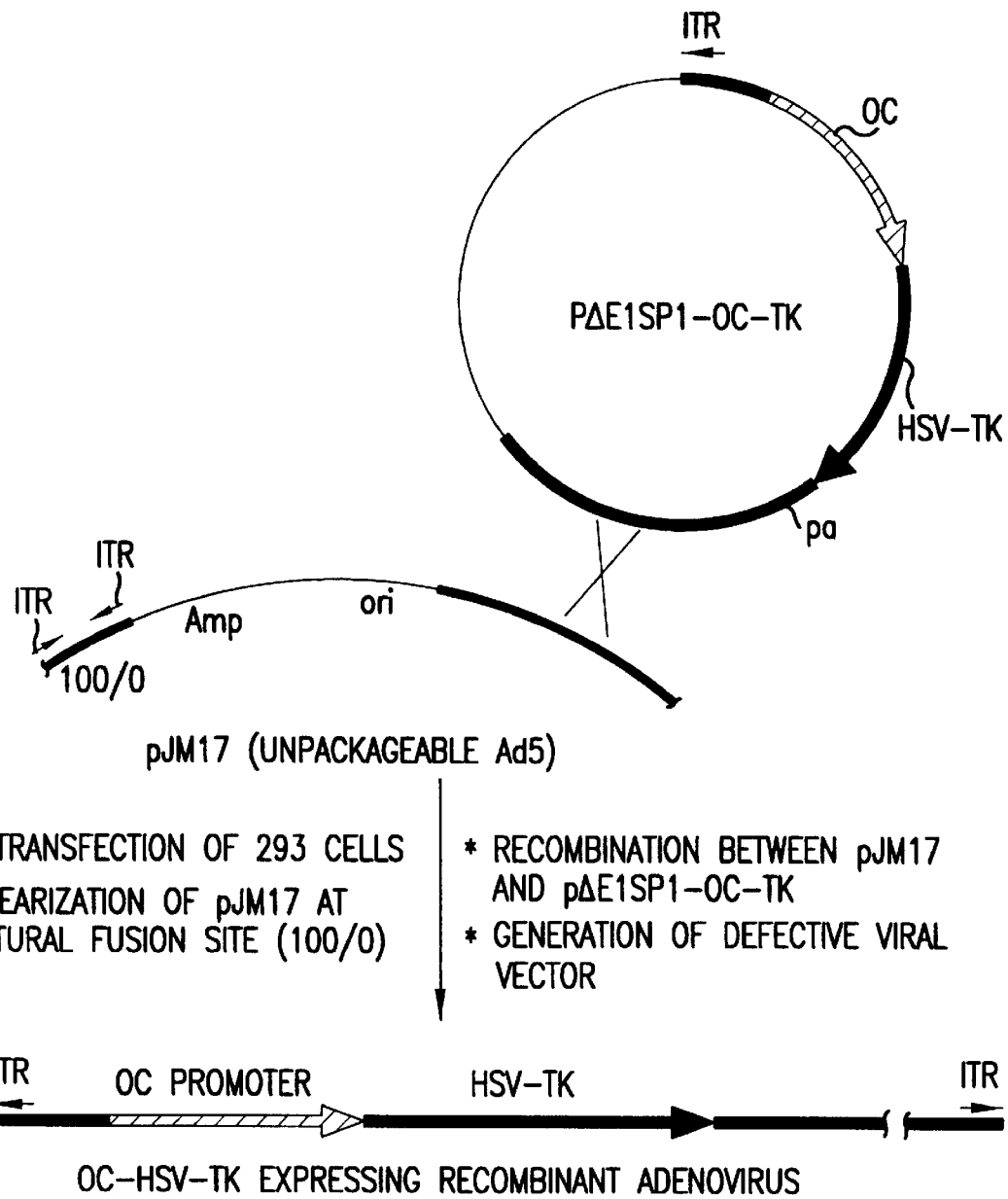
FIG. 1 depicts the construction of Ad-OC-TK, a recombinant adenovirus vector, containing the osteocalcin (OC) promoter driven toxic thymidine kinase (TK) gene. An expression clone PΔESP1-OC-TK and pJM17 was cotransfected 293 cells, then recombinant Ad-OC-TK was generated and plaque purified.

The abbreviations used throughout the specification and Figures are as follows:

TK, thymidine kinase; OC, osteocalcin; Ad, adenovirus; ACV, acyclovir; FBS, fetal bovine serum; RSV, Rous sarcoma virus; β-tal, β-galactosidase; CMV, cytomegalovirus; GCV, ganciclovir; X-tal, 5-bromo-4-chloro-3-indolyl-βgalactopyranoxide; MOI, multiplicity of infection(s); ROS, rat osteoblastic osteosarcoma; MG 63, human osteosarcoma; SK-N-SH, human neuroblastoma; A172, human glioblastoma; H4, human neuroglioma; HS 683, human glioma; TLB-G, human normal glia; CH-157MN, human meningioma; HOG, human oligodendroglioma; TC620, human normal oligodendrocyte; WH, human bladder cancer; 3T3 NIH, human fibroblasts.

DESCRIPTION OF THE PREFERRED EMBODIMENT

The present invention provides for a therapeutic agent comprising a recombinant adenovirus (Ad) vector containing an osteocalcin (OC) promoter driven toxic thymidine kinase (TK) hereinafter represented by the formula:

AD-OC-TK

In another aspect of the present invention there is provided a method for treating a tumor comprising delivering a therapeutic agent to a tumor. The therapeutic agent comprises a recombinant adenovirus vector (Ad) containing an osteocalcin promoter driven toxic thymidine kinase (TK).

In an additional aspect of the present invention a method for treatment of a tumor is provided which comprises delivering to the tumor a therapeutic agent containing a recombinant adenovirus (Ad) vector containing an osteocalcin (OC) promoter driven toxic thymidine kinase (TK) in combination with acyclovir (ACV).

It is preferred that the therapeutic agent containing the Ad-OC-TK, in the presence or absence of ACV, be administered to osteosarcoma tumors, prostate and breast cancers, brain tumors, and their metastases to the lung, or osseous metastatic tumors such as melanoma, prostate or breast tumors In another aspect of the present invention therapeutic application of Ad-OC-TK is provided to target cancers that metastasize to the lung and the skeleton. Whereas, osteosarcoma metastasize frequently to the lung, prostate cancer, breast cancer, and rare ocular melanomas metastasize prevalently to the bone and elicit either an osteoblastic or an osteolytic reaction.

Applicants have unexpectedly discovered that Ad-OC-TK-infected osteosarcoma cell lines of the osteoblast cell lineage (e.g, ROS and MG-63 cells) expressed high levels of thymidine kinase (TK) activity while cell lines not of the osteoblast lineage, such as WH and NIH 3T3, expressed low TK activity. Further, Applicants have unexpectedly discovered that consistent with measured TK activity, the addition of acyclovir (ACV), a pro-drug substrate for TK, followed by Ad-OC-TK infection inhibited the growth of osteosarcoma cells lines in vitro and also sarcoma xenografts in vivo. The growth of WH and NIH 3T3 cells was not effected by Ad-OC-TK either with or without ACV administration. Thus, Applicants have unexpectedly discovered that Ad-OC-TK constitutes a tumor-specific toxic gene therapy that inhibits the growth of proliferating osteosarcoma cells and spares significant tissue damage in the surrounding non-proliferating normal tissues and cells that are of non-osteoblastic lineage. Further, the osteocalcin (OC) promoter-mediated gene delivery system is superior to conventional gene therapy in which TK expression is driven by universal promoters such as cytomegalovirus (CMv; promoter and the long terminal repeat promoters from Rous sarcoma virus (RSV) or moloney murine leukemia.

Further, Ad-OC-TK, when delivered concurrently with ACV, is highly effective in inhibiting the growth of both murine and human osteosarcoma cell lines in vitro and murine osteosarcoma in vivo.

As mentioned above another potential therapeutic application of Ad-OC-TK is to target cancers that may metastasize to the lung and the skeleton. Although Applicants do not wish to bind themselves to any specific theories, they believe a possible mechanism for malignant cell recruitment to lung or bone is that osteosarcoma cells may have special affinity to deposit and grow in lung parenchyma and fibromuscular stromal network whereas osteogenic cells may synthesize and secrete products that are able to stimulate the growth, adhesion, and migration of the prostate or breast cancer cells. For the osteosarcoma patients, Ad-OC-TK is expected to have a direct cytotoxic effect on the growth primary as well as metastatic osteosarcoma based upon data obtained from experimental models. The proliferation and migrating of prostate or breast tumor cells may secrete paracrine growth factors that stimulate osteoblast or osteoclast cell growth at sites of bone metastases that resulted in the induction of predominantly osteoblast (e.g., prostate cancer) or osteolytic (e.g., breast cancer) reactions in the skeleton. Since tumor cell growth is intimately affected by the surrounding stroma and reciprocal interactions exist between the growth of certain tumors (e.g., prostate and breast) and bone stroma, the development of a Ad-OC-TK is a new gene therapy modality for prostate or breast cancer patients. Thus, Ad-OC-TK therapeutic gene exhibits additional therapeutic implications: (a) Ad-OC-TK could block not only the growth of osteosarcoma but also eradicate osteoblastic cells that may be required to maintain the survival of osseous metastatic tumors such as prostate or breast tumors; although Ad-OC-TK may also eradicate the growth of normal osteoblasts, this appears not to be of concern because transgenic mouse bearing OC-TK treated with ACV did not affect their survival; (b) Ad-OC-TK could express high levels in a large number of calcified tumors and normal tissues. Thus, Ad-OC-TK plus ACV is a reasonable choice for eradicating the group of a primary tumor and its metastasis and normal calcified tissues such as atherosclerotic plaques; (c) Ad-OC-TK may be used in conjunction with conventional chemotherapy and radiation therapy in reducing tumor burden and pain associated with local tumor growth as well as osseous metastases; and (d) long-lasting anti-tumor immunity might be elicited against the remaining osteoblastic cells from TK-induced killing of tumor cells.

In addition, Ad-OC-TK was injected into syngeneic or athymic mice bearing osteosarcoma metastases in the lung and have observed marked reduction of tumor burden in the lung as evaluated by the wet weight of the lung.

Prostate cancer metastasizes primarily to the skeleton. Applicants have demonstrated that osteocalcin (OC) promoter drives the expression of therapeutic toxin gene Herpes Simplex Virus (HSV), thymidine kinase (TK), in osteoblast and nonosteoblast cell types, including androgen-dependent and androgen-independent prostate cancer cells.

Applicants have shown that Ad-OC-TK virus plus ACV treatment is highly selective in blocking the growth of human prostate cancer in vitro and in vivo.

Relevant documents reflecting the inventors' own work, and not prior art, include Ko et al, Human Gene Therapy, 7:1683–1691 (Sept. 1996) and Ko et al., Cancer Research 56, 4614–4619 (October, 1996).

Applicants have further developed an OC promoter-based suicide gene therapy, driven by vitamin $D_3$, analogs, to kill both androgen-dependent and androgen independent prostate cancer cells and their supporting stroma. Although Applicants do not want to bind themselves to any theory they believe that Vitamin $D_3$ analogs appear to have dual action in promoting prostate cancer differentiation (inhibiting prostate cancer proliferation) and drive the expression of therapeutic toxic genes in both cancer epithelium and bones stroma.

Thus, a novel therapeutic agent comprising a recombinant Ad-OC-TK virus was generated. Further, a method is provided where the novel therapeutic agent Ad-OC-TK can selectively target and induce the killing of osteoblast lineage cells and a wide spectrum of tumor cells that have the ability to calcify either at the primary or at distant metastases.

Further, a new recombinant Ad-OC-TK therapy agent is provided for osteosarcoma patients as well as for patients with melanoma, brain tumors, tumors metastasized to the lung and osseous metastatic tumors such as melanoma, breast cancer, or prostate cancer.

Other toxins may be substituted for TK. Genes for cytosine deaminase, p53 tumor suppressor gene, and cyclic regulatory proteins, including various cytokines, and others, e.g., p16, p21 can be used in this invention in place of TK genes.

Having generally described this invention, a further understanding can be obtained by reference to certain specific examples which are provided herein for purpose of illustration only and are not intended to be limiting unless otherwise specified.

EXAMPLES

Cells and Cell Culture.

ROS 17/2.8, a rat osteoblastic osteosarcoma cell line, which is obtained by harvesting cells from tumor explants grown in culture (ROS 17/2.8 was obtained from the University of Texas Dental Branch, Houston, Tex.). MG-63, a human osteoblast-derived osteosarcoma cell line; 293, a transformed human embryonic kidney cell line; and NIH 3T3, an embryonic mouse fibroblast cell line, were purchased from American Type Culture Collection (Rockville, Md.). WH, a human bladder transitional cell carcinoma, was established by our laboratory (described in Gleave, M. E., Haich, J. T., Wu, H. C., Hong, S. J. Zhau, H. E., Guthrie, P. D., and Chung, L. W. K. Epidermal growth factor receptor-mediated autocrine and paracrine stimulation of human transitional cell carcinoma. Cancer Res., 53: 5300–5307, 1993). The ROS 17/2.8 and MG-63 cell lines are considered the osteoblast lineage because of their morphological, biochemical, and molecular characteristics, they were incubated in DMEM (Life Technologies, Inc., Grand Island, N.Y.) and 20% F12K (Irving Scientific, Santa Ana, Calif.) supplemented with 100 units/ml penicillin, 100 $\mu$/ml streptomycin, and 10% FB5 (Sigma Chemical Co., St. Louis, Mo.). The WH and NIH 3T3 cell lines were maintained in T medium, (as described in Ko, S-C., Gotoh, A., Thalmann, G. N., Zhou, H. E., Johnston, D. A., Zhang, W. W., Kao, C., and Chung, L. W. K. Molecular therapy with recombinant p53 adenovirus in an androgen independent, metastatic human prostate cancer model. Hum. Gene Ther., 7: 1683–1691, 1996), containing 5% FBS (fetal bovine serum). The 293 cells were maintained in MEM (Life Technologies, Inc.) with 10% FBS and 1% tryptose phosphate broth (Life Technologies, Inc.). The cells were fed three times a week with fresh growth medium unless otherwise indicated.

Construction and Large-scale Production of a Recombinant Ad Vector Containing the OC Promoter-TK.

Construction of the recombinant Ad-OC-TK virus was accomplished as shown in FIG. 1. All plasmids were constructed according to standard protocols. Briefly, pAE1SP1, a shuttle vector which contains the 5' end part of the adenovirus genome with E1-region deleted, was digested with Xho-1 (New England Biolabs, Beverly, Mass.) and treated with alkaline phosphatase (Boehringer Mannheim Biochemicals, Indianapolis, IN) according to the supplier's protocols. The Xho-1-digested 3.1-kb fragment containing the murine OC promoter (1.3 kb)-driven TK (1.8 kb) construct was generated from pII1.5 plasmid and ligated into pΔE1SP1 Ad vector using T4 ligase (New England Biolabs).

The recombinant shuttle vector, p2ΔE1SP1-OC-TK, is co-transfected with pJM17, a circular adenovirus genome (with E1 region deleted and replaced with PBR322 DNA) purified from adenovirus infected cells, into 293 cells by the N-[1-(2,3-dioleoyloxyl)propyl]-N,N,N-trimethylammoniummethyl sulfate (Boehringer Mannheim Biochemicals)-mediated transfection method, Zhang, W-W., Fang, X., Branch, C. D., Mazur, W., French, B. A., and Roth, J. A. Generation and identification of recombinant adenovirus by liposome-mediated transfection and PCR analysis, Biotechniques, 15:868–872, 1993. The culture medium of the 293 cells showing the completed cytopathic effect was collected and centrifuged at 1000×g for 10 minutes. The pooled supernatants were aliquoted and stored at −80° C. as primary viral stock. Viral stocks were propagated in 293 cells, and selected clones of Ad-OC-TK virus were obtained by plaque purification according to the method of Graham and Prevec, Graham, F. L., and Prevec, L. Manipulation of adenovirus vectors, Vol. 7, pp.109–128. Clifton, N.J.: The Humana Press, Inc., 1991. One of the viral clones was propagated in 293 cells; cells were harvested 36 to 40 hours after infection, pelleted, resuspended in PBS, and lysed. Cell debris was removed by subjecting the cells to centrifugation, and the virus in the cell lysate was purified by $CsCl_2$ gradient centrifugation. Concentrated virus was dialyzed, aliquoted, and stored at −80° C. The viral titer was determined by plaque assay. The control viruses used in this study, Ad-RSV-β-Gal and Ad-CMV-β-Gal, were constructed in a similar manner (described in Ko, S-C., Gotoh, A., Thalmann, G. N., Zhou, H. E., Johnston, D. A., Zhang, W. W., Kao C., and Chung, L. W. K. Molecular therapy with recombinant p53 adenovirus in an androgen independent, metastatic human prostate cancer model. Hum. Gene Ther., 7: 1683–1691, 1996)

X-Gal Staining of Ad-RSV-β-Gal Virus-Infected Cells.

ROS, MG-63, WH, and NIH 3T3 cells, after infected with various doses of recombinant Ad-RSV-β-Gal, were grown in 60-mm dishes to about 80–90% confluency for 2 days, then the medium was discarded and fixed with 0.05% glutaraldehyde. After discarding the fixative solution, cells were rinsed thoroughly three times in PBS at room temperature. An X-Gal solution mixture [0.5 ml; 35 mM $K_3Fe(CN)_6$; 35 mM $K_4Fe(cCN)_6$, $3H_2O$, 1 mM $MgSO_4$, and 1 mg/ml X-Gal (Sigma Chemical Co.)] was added to cover cells. Cells were then incubated 1 hour to overnight at 37° C. Positive cells were stained blue, and the percentage of blue cells was calculated.

Determination of TK Activity In Target Cells Infected with Ad-OC-TK.

Crude cell extracts containing TK were prepared from Ad-OC-TK-infected ROS, MG-63, WH, and NIH 3T3 cells. Briefly, cells were cultured in 100-mm dishes in 60 to 70% confluency, at which point they were exposed to 20 MOI (multiplicity of infections) of Ad-OC-TK overnight. The culture medium was then replaced with fresh medium after overnight infection, and the replaced culture medium was removed after an additional 48 hours incubation. The infected cells were washed with PBS, trypsinized, and then counted; the expressed TK enzymatic activity was recovered from cells by the repeated freeze and thaw method. The resultant cell suspension was centrifuged at 300×g for 10 minutes, and the supernatant fraction was frozen at −80° C. for TK activity assay. TK activity was assayed by phosphorylation of [$^3$H]GCV, as described previously, Graham and Prevec, Graham, F. L., and Prevec, L. Manipulation of adenovirus vectors, Vol. 7, pp.109–128. Clifton, N. J.: The Humana Press, Inc., 1991, with modification. Briefly, the supernatant fraction harvested from approximately 1×10$^6$ cells containing TK was mixed with an equal volume of TK assay buffer containing 0.2 µCl of [$^3$H]GCV (10 µm; Moravek Biochemicals, Brea, Calif.), 3 mM MgCl$_2$, 3 mM ATP (adenosine triphosphate), 10 µg/µl BSA (bovine serum albumin), and 50 mM sodium phosphate buffer (pH 6.5). The reaction mixture was incubated in a 36° C. water bath for 90 minutes and the reaction mixture was transferred onto DE-81 discs (Whatman, Hillsboro, Oreg.), air-dried, and washed thoroughly with 50% ethanol. Phosphorylated [$^3$H] GCV bound to the filter discs was determined with a scintillation counter (Beckman Instruments, Inc., Schaumburg, Ill.). GCV, a substrate for TK, differs from ACV (Burroughs Wellcome, Research Triangle, N.C.) structurally only by the addition of a hydroxymethyl group. Because of this one side chain difference, GCV is administered only through an i.v. route, whereas ACV can be administered p.o., i.v., and topically to humans, ACV and GCV are both commonly used clinically against herpes virus infection. In this communication, because of the availability and rate of absorbency, [$^3$H]GCV is used to assay TK activity assay, whereas ACV is used for both the in vitro and in vivo studies.

Acyclovir in Vitro Cytotoxicity Assay.

To determine ACV dose-response curves, ROS, MG-63, WH, and NIH 3T3 cells were plated in 24-well Falcon tissue culture plates (Falcon Products, Franklin Lakes, NJ) and exposed to various concentrations of ACV ranging from 10 to 1000 µgml media. Cell numbers were measured daily by the crystal violet assay using an automated Emax spectrophotometric plate reader (Molecular Devices Corp., Sunnyvale, Calif.).

Ad-OC-Tk plus ACV-induced in Vitro Cytotoxicity Assay.

ROS, MG-63, WH, and NIH 3T3 cells were seeded onto 24-well plates at a density of 5.0×10$^3$ cells/well. After 24 h, the cells were infected with FBS (fetal bovine serum), or Ad-OC-TK at a concentration of 20 MOI (multiplicity of infection) for 8 h. Following infection the medium containing Ad-OC-TK was replaced with fresh medium containing 0 or 10 µg/ml ACV with daily medium changes for an accumulated period of 7–9 days. The cell number per well was assessed by crystal violet assay as described above.

Ad-OC-TK and ACV-induced Inhibition of Tumor Growth in Vivo.

Congenitally athymic nude (nu/nu) mice (Harlan Co., Houston, Tex.) 5 to 6 weeks of age, were inoculated s.c. with ROS (3×10)cells, a rat osteosarcoma cell line. When the tumor became palpable (4–5 mm in diameter), the animals were randomly assigned to three experimental groups: group 1, ACV only; group 2, Ad-OC-TK only; and group 3, Ad-OC-TK plus ACV. For Ad-OC-TK injection, a microliter syringe fitted with a 28gauge needle was used to deliver 75 µl of Ad-OC-Tk (1×10$^9$ plaque-forming units). The Ad-OC-TK was injected intratumorally along both the long and short axes of the tumor; one injection parallel to the long axis, and one perpendicular to the axis. The needle point was then rotated within the tumor to maximize the area of Ad delivery, Ad-OC-TK was injected every other day for a total of three doses. Tumor volume was calculated by the following formula: volume (a rotational ellipsoid) =$M_1 \times M_2^2 \times$ 0.5236 ($M_1$, long axis; $M_2$, short axis; Ko. S.-C., Gotoh, A., Thalmann, G. N., Zhou, H. E., Johnston, D. A., Zhang, W. W., Kao, C., and Chung, L. W. K. Molecular therapy with recombinant p53 adenovirus in an androgen independent, metastatic human prostate cancer model. Hum. Gene Ther., 7: 1683–1691, 1996). Acyclovir (ACV) treatment only or Ad-OC-TK plus ACV experimental groups were treated with an i.p. injection of ACV at a dose of 40 mg/kg body weight daily for 7 days. Ad-OC-Tk and/or ACV treatment did not adversely affect the body weight of experimental animals. Tumor volume was calculated every other day for the first 8 days on day 20 and day 32.

Adenoviral Transduction Efficiently to ROS and MG-63 Cells and TK Expression in Vitro.

To test the efficiency of Ad infection in ROS, a rat osteogenic sarcoma cell line, and in Mg-63, a human osteosarcoma cell line, we used a recombinant adenoviral vector containing the RSV-β-Gal expression cassette (Ad-RSV-β-Gal). Based upon X-Gal staining of β-Gal activity, a dose-dependent increase of Ad infection was noted in ROS and MG-63 cells, with the percentage of cells infected gradually 6, 75, and 100as the adenoviral MOI increased 20, 40, and 60 MOI per target cell. A similar efficiency of adenoviral infection was observed in WH and NIH 3T3 cells. In comparison to uninfected control cells, mild cytotoxicity was noted through the application of Ad up to 60 MOI.

Figure 2:
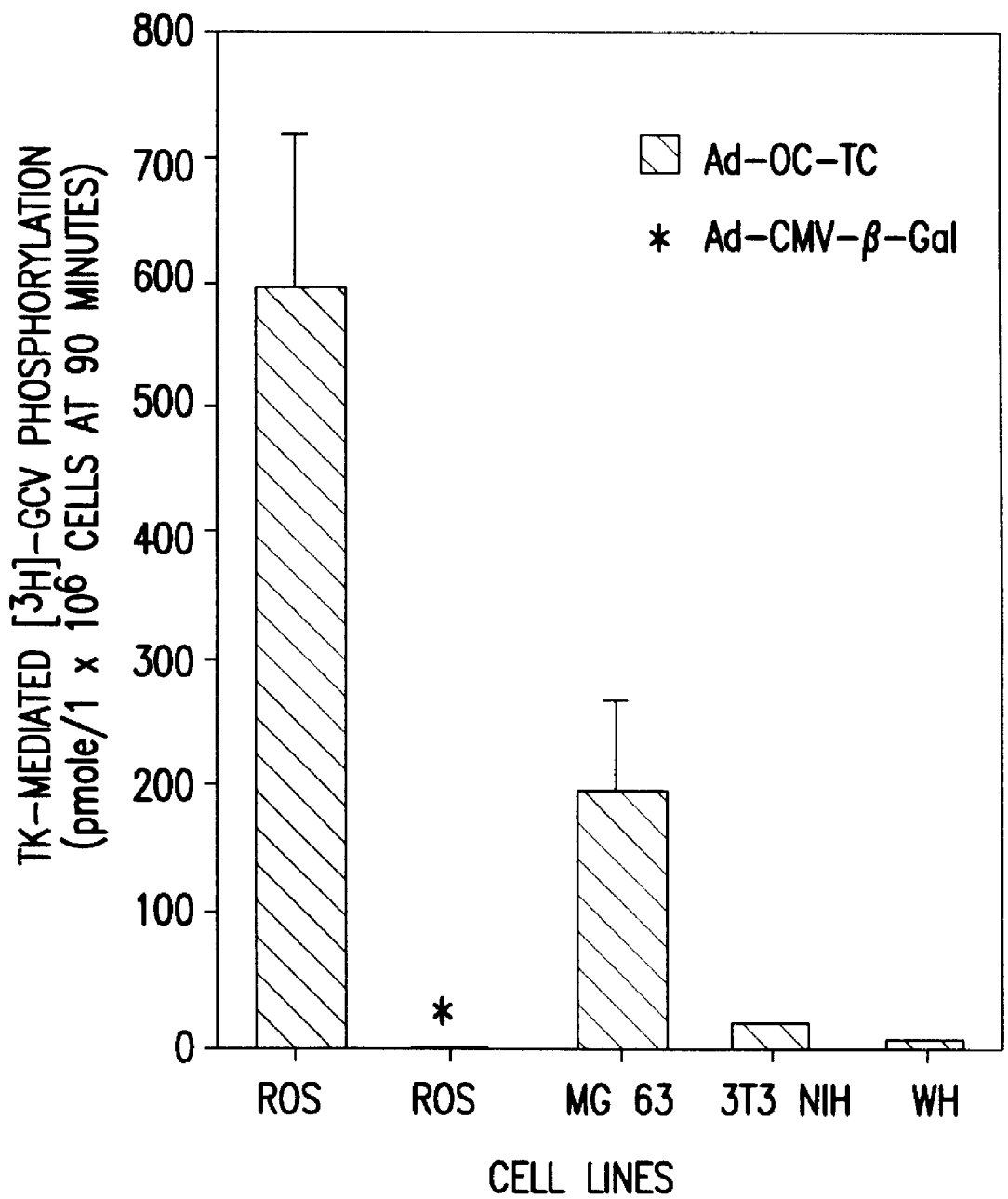
FIG. 2 depicts determination of thymidine kinase (TK) activity in target cells infected with Ad-OC-TK. Cells were exposed to Ad-OC-TK (20 Mols per target cell), and their crude cellular lysate was obtained and assayed for TK activity. The mean TK activity was significantly higher in osteosarcoma ROS and MG-63 cells than in the WH and NIH 3T3 cell lines. Thymidine Kinase activity in ROS cells following infection with Ad-CMV-B-Gal was used as a negative control.

To assess whether Ad-OC-TK may drive the expression of the TK gene in a cell type-specific manner, ROS, MG-63, WH, and NIH 3T3 cells were exposed to Ad-OC-TK (20 MOI/target cell), and their crude cellular lysates were obtained and assayed for TK activity. TK activity was indirectly determined by measuring the amount of phosphorylated [$^3$H]GCV phosphorylation (i.e., TK activity) per 10$^6$ cells was significantly higher in osteosarcoma ROS and MG-63 cells than in the WH and NIH 3T3 cell lines (FIG. 2). TK activity in ROS cells following infection with 20 MOI of Ad-CMV-β-Gal, Ko. S-C., Gotoh, A., Thalmann, G. N., Zhou, H. E., Johnston, D. A., Zhang, W. W., Kao, C., and Chung, L. W. K. Molecular therapy with recombinant p53 adenovirus in an androgen independent, metastatic human prostate cancer model. Hum. Gene her., 7: 1683–1691, 1996 serves as a negative control.

Cytotoxicity of ACV in Ad-OC-TK-transduced ROS and MG-63 Cells in Vitro.

Figure 3A:
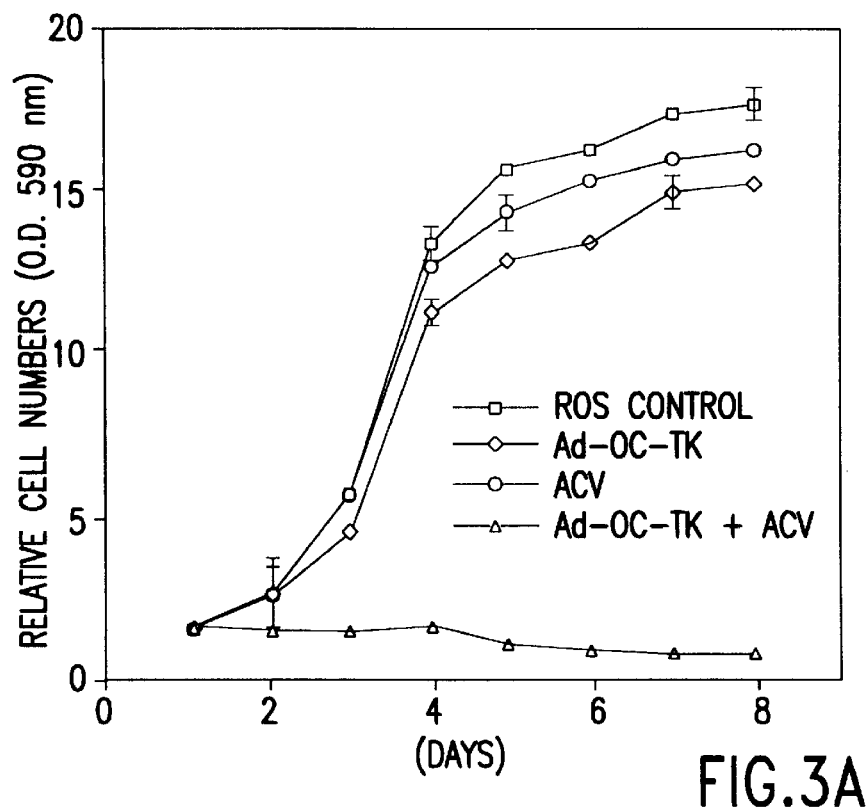
FIG. 3 depicts cytotoxicity of ACV in AD-OC-TK transduced osteoblastic ROS and MG-63 cells in vitro. The growth of murine osteogenic ROS (FIG. 3, Panel A) and human osteosarcoma MG-63 (FIG. 3, Panel B) cells, infected with 20 Mols of AD-OC-TK, was significantly inhibited by the addition of acyclovir (ACV) (10 µg/ml). Consistent with low levels of TK activity, the growth of WH (FIG. 3, Panel C) and NIH 3T3 (FIG. 3, Panel D) cells after AD-OC-TK infection was not affected by the addition of ACV in the tissue culture medium.
Figure 3B:
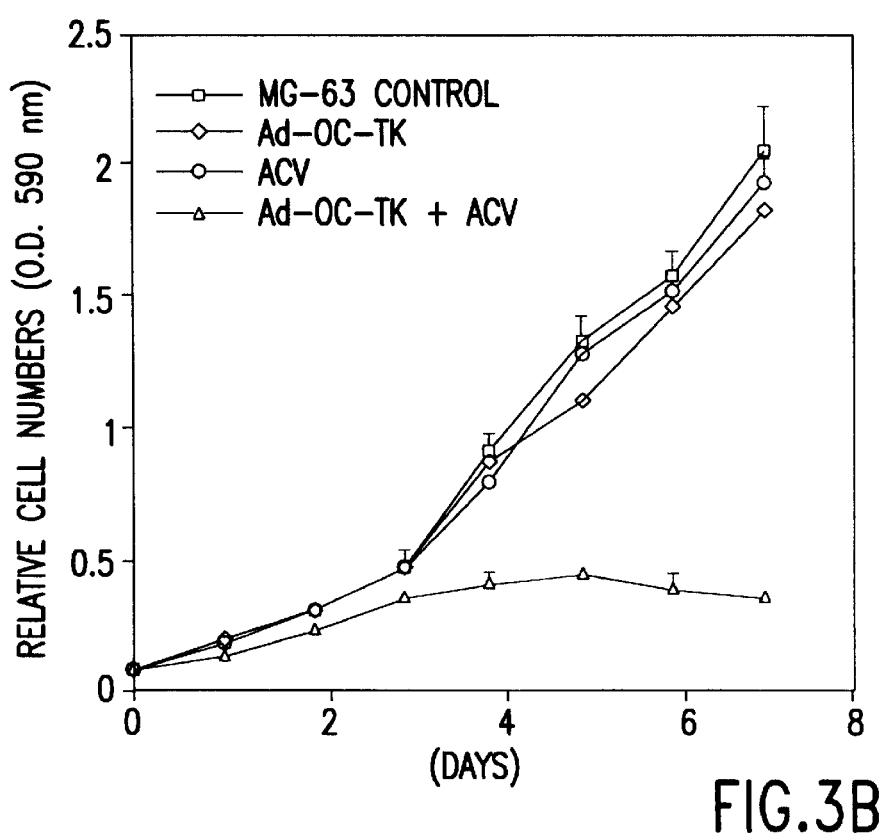
Figure 3C:
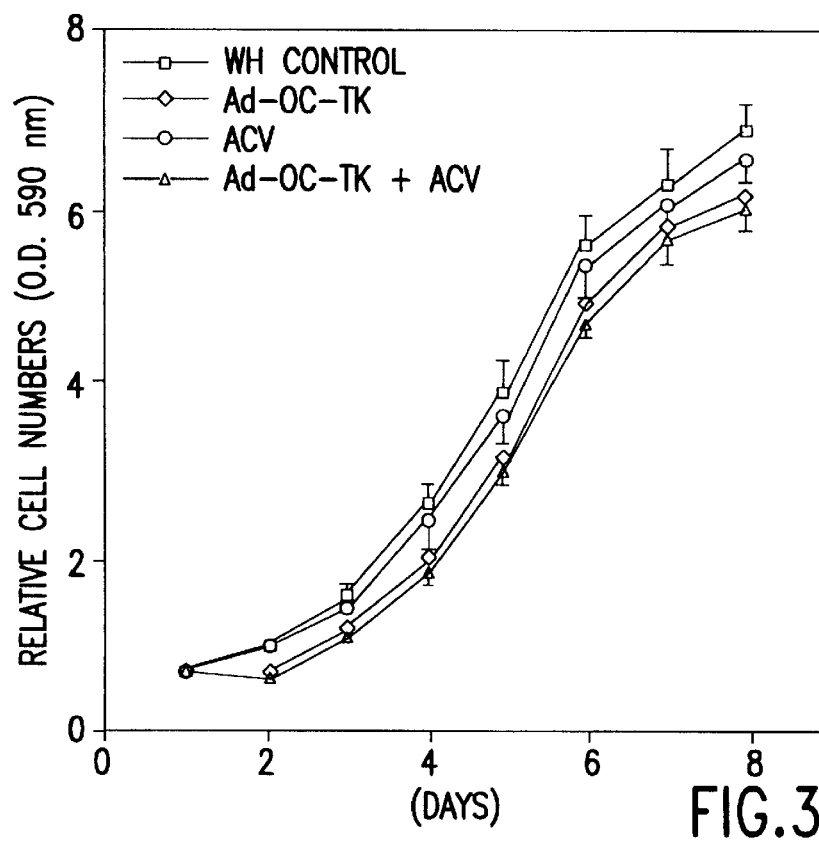
Figure 3D:
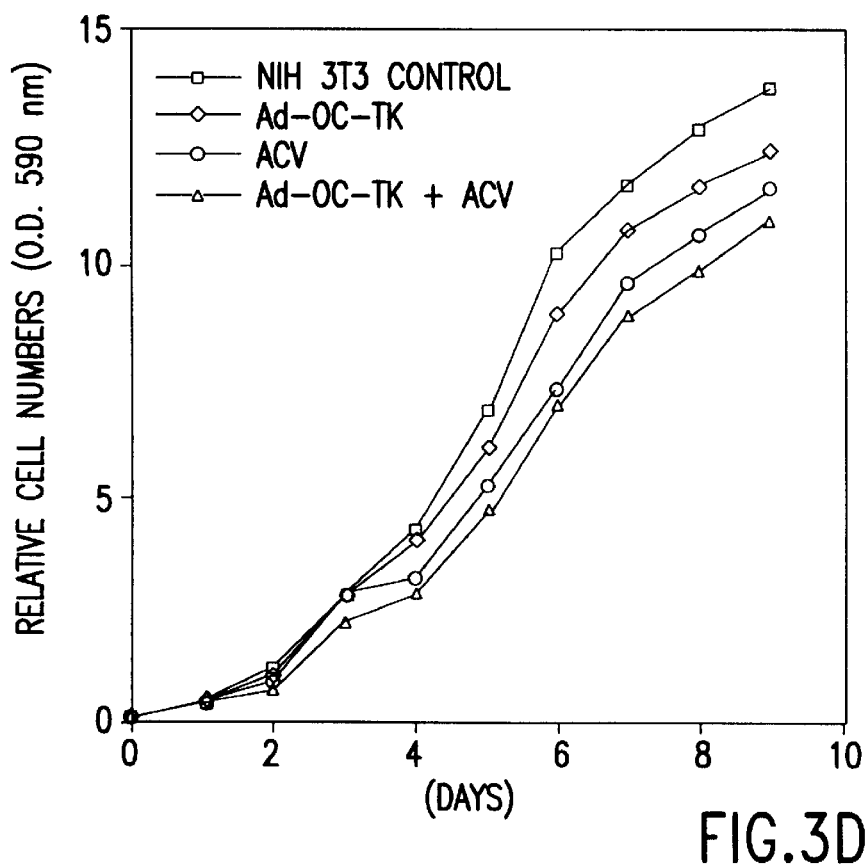

To determine whether Ad-mediated transduction with the OC-TK gene would render ROS or MG-63 cells sensitive to cell killing by ACV, we first tested the toxicity of ACV (range, 0–1000 µg/ml) in non-infected ROS, MG-63, WH, and NIH 3T3 cells and observed that ACV at doses below 40 µg/ml did not appreciably inhibit the growth of all cell lines tested (data not shown). The growth of ROS (FIG. 3A) and MG-63 (FIG. 3B) cells, infected with 20 MOI of AD-OC-TK, was significantly inhibited by the addition of ACV (10 TK; cells infected with Ad-OC-TK (20 MOI/target cell) or treated with ACV (10 µg/ml) alone did not exhibit altered growth or morphology during a 7–9 day observation period. Consistent with the low levels of TK activity, the growth of WH (FIG. 3C) and NIH 3T3 (FIG. 3D) cells after Ad-OC-TK infection was not affected by the addition of pro-drug ACV in the cell culture medium. Similarly, Ad-OC-TK or ACV alone did not affect proliferation in these cells.

Cytotoxicity of ACV in Ad-OC-TK-infected ROS Tumor Growth in Vivo.

Figure 4:
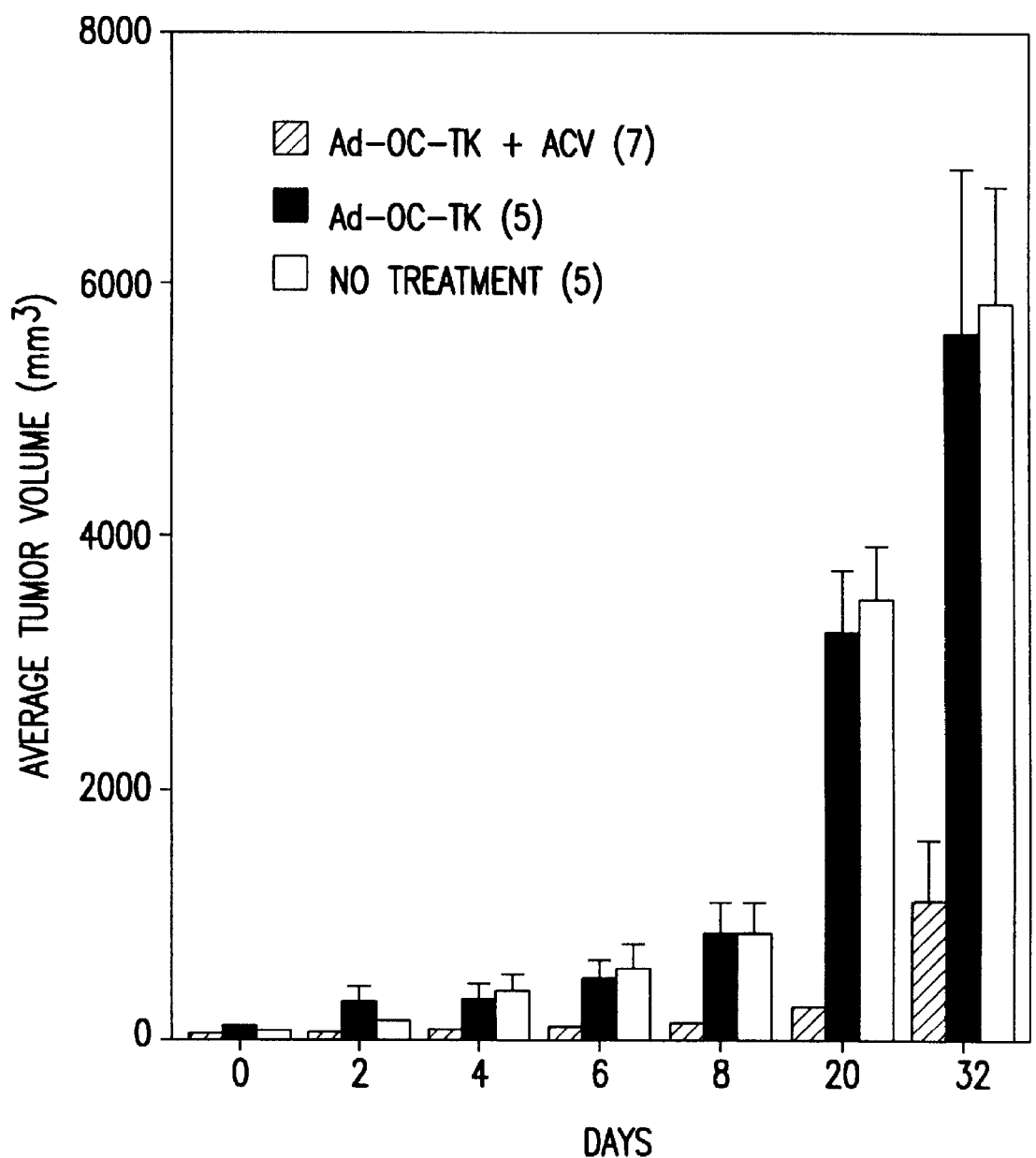
FIG. 4 depicts cytotoxicity of ACV in AD-OC-TK infected ROS tumor growth in vivo. ACV markedly suppressed the growth of ROS tumors following AD-OC-TK infection; AD-OC-TK infected ROS sarcomas or ACV treatment of tumor xenografts alone did not affect the rate of tumor growth.
Figure 5:
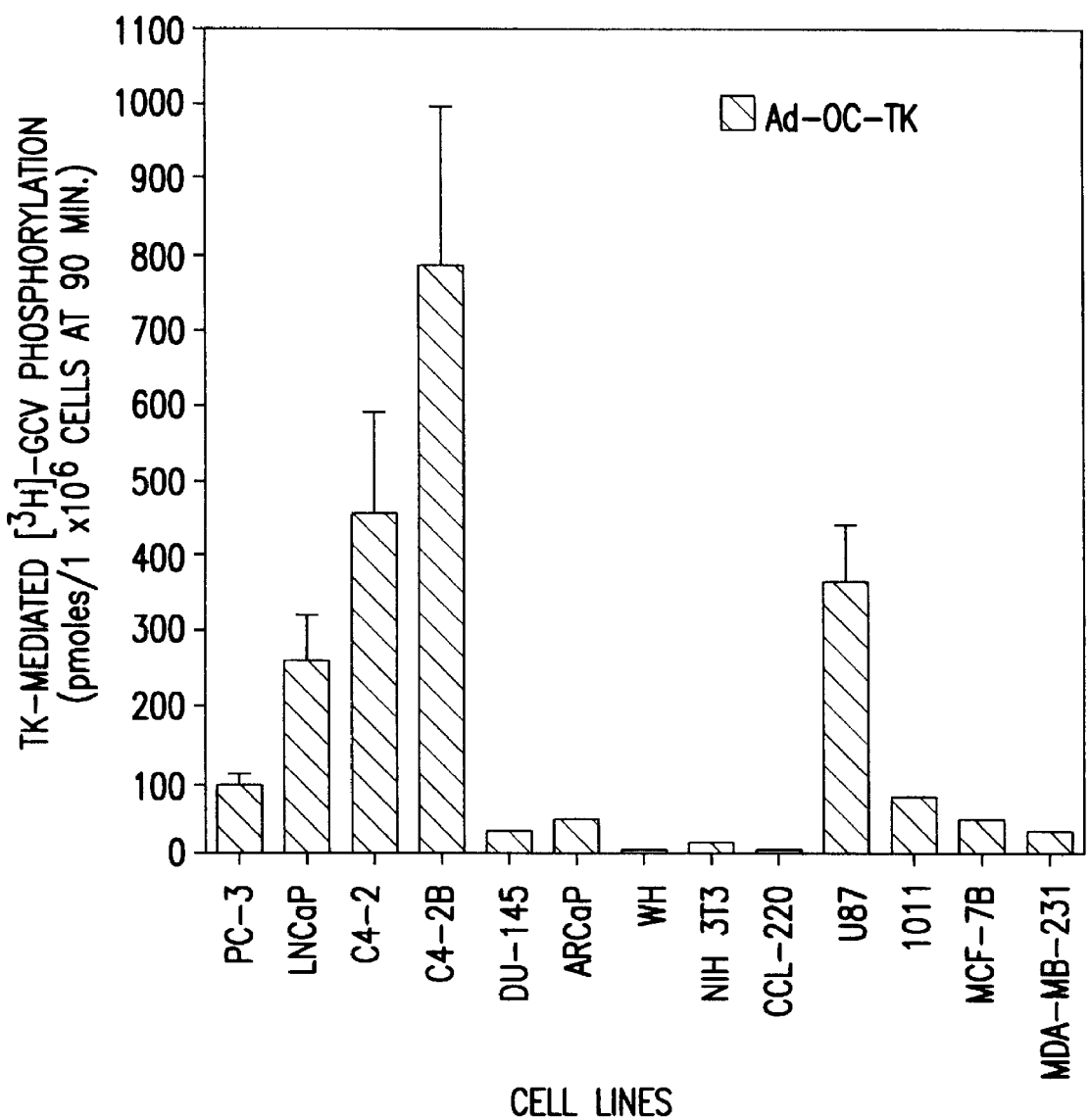
FIG. 5 depicts cell-specificity of expression of AD-OC-TK. Androgen-dependent (LNCaP), androgen-independent (PC-3, C4-2, C4-2B, DU-145, and ARCAP) prostate cancer cell lines, glioma (U87), melanoma (1011) and breast (MCF-7B and NOA-MB-231) cancer cells expressed TK activity as assayed by the phosphorylation of [$^3$H]-GCV; low activity was detected in human bladder transitional cell carcinoma NM and a lung fibroblast cell line CCL-220. In other studies, it was shown that OC mRNA was expressed by a human lung cancer cell line.
Figure 6A:
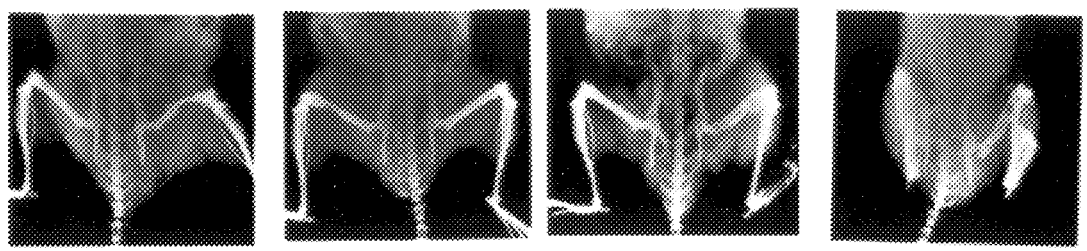
FIG. 6 depicts effect of AD-OC-TK and acyclovir (ACV) in blocking PC-3 tumor growth in the skeleton. Mice were inoculated intra-osseously PC-3 tumor cells. 20 days after tumor cell inoculation, the animals were treated intra-osseously with AD-OC-TK and ACV. Note four treated animals had tumor regression in comparison to the four untreated animals which develop extensive osteolytic lesions and destruction of the bone.
Figure 6B:
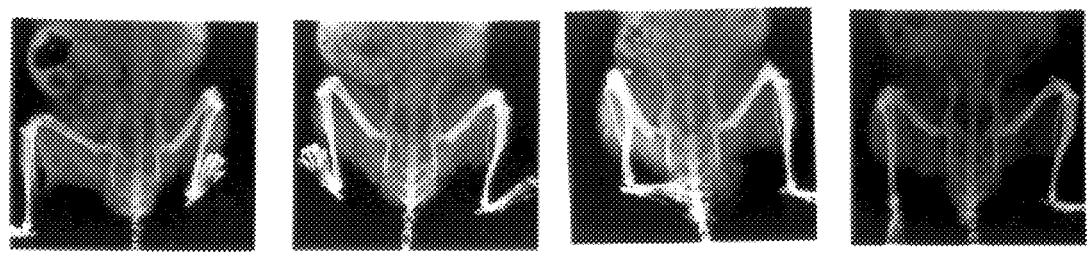
Figure 7:
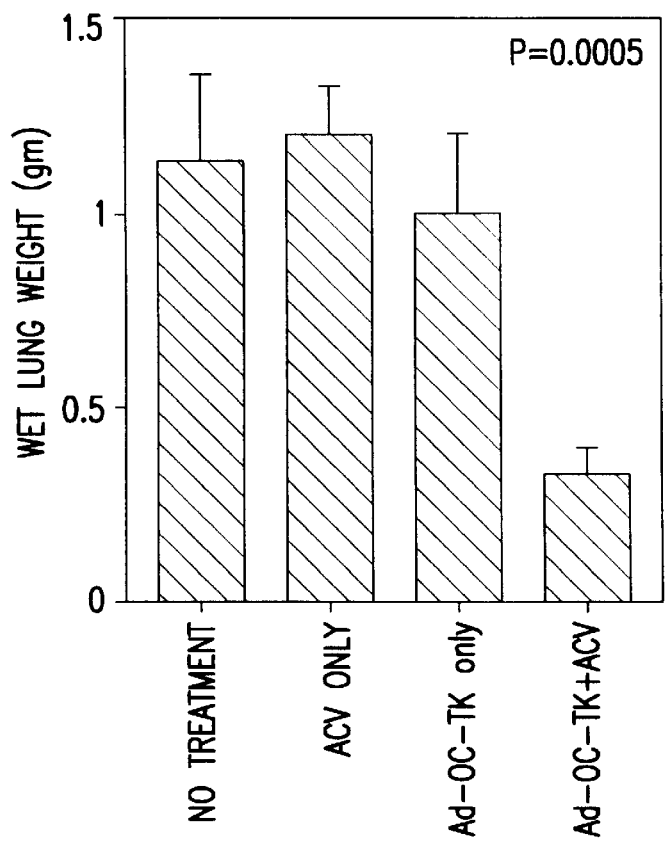
FIG. 7 depicts wet lung weight in athymic mice treated with Ad-OC-TK, ACV, or combined Ad-OC-TK+ACV. Note: Ad-OC-TK and ACV combined treatment markedly decreased wet lung weight in athymic mice injected intravenously with ROS sarcoma cells. In this study, it was determined that lung weight correlated proportionately with tumor burden.
Figure 8:
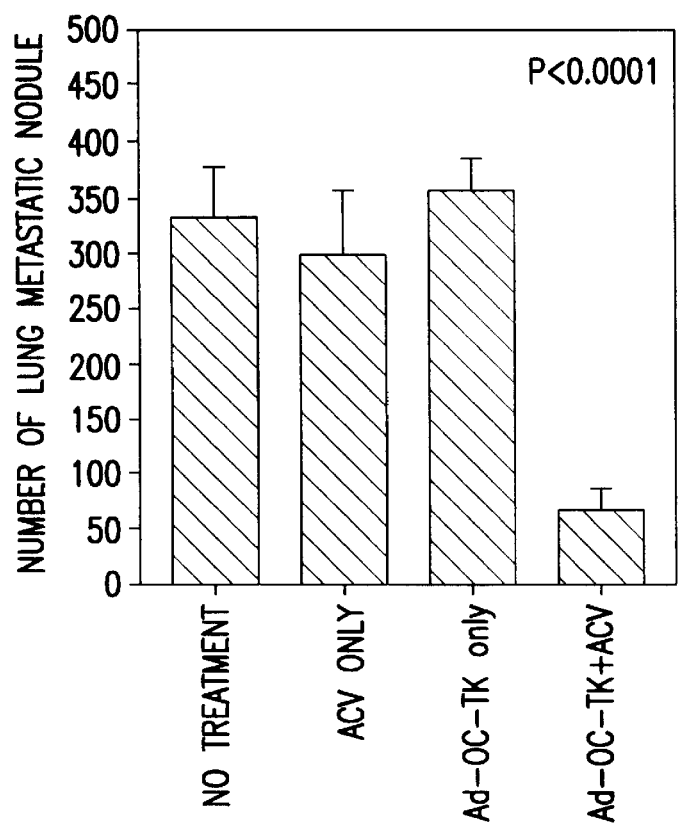
FIG. 8 depicts number of lung metastatic nodules in mice treated with ACV, Ad-OC-TK, or combined Ad-OC-TK+ACV. Note: Number of lung metastatic nodules were greatly decreased by combined treatment of Ad-OC-TK+ACV.
Figure 9:
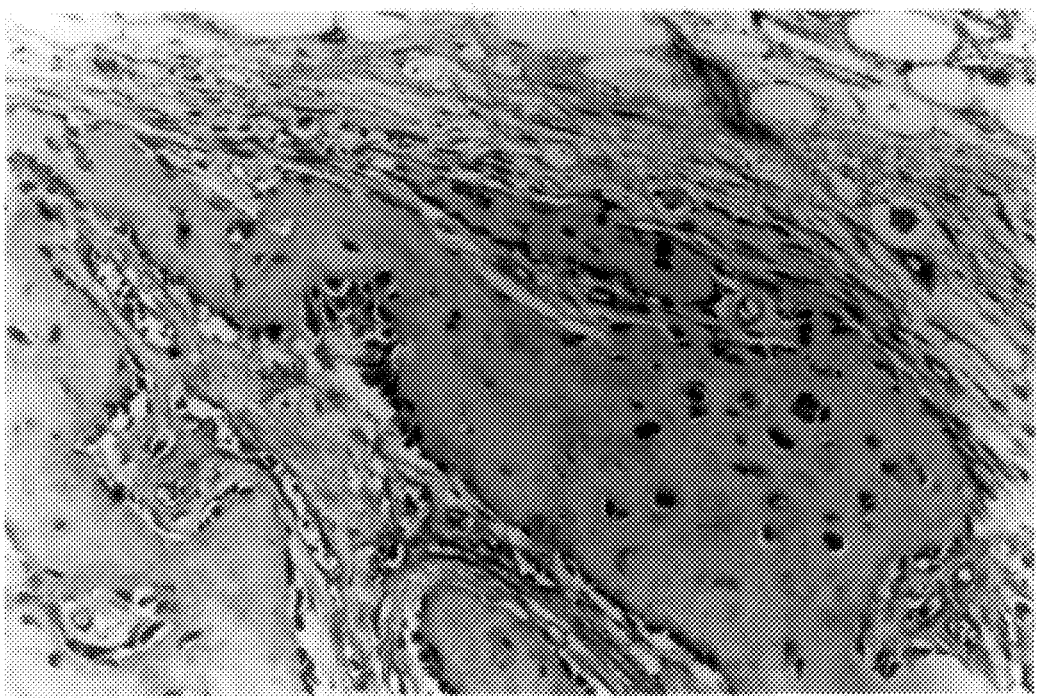
FIGS. 9 to 16 show immunohistochemical staining of human tissues with osteocalcin antibody.
Figure 10:
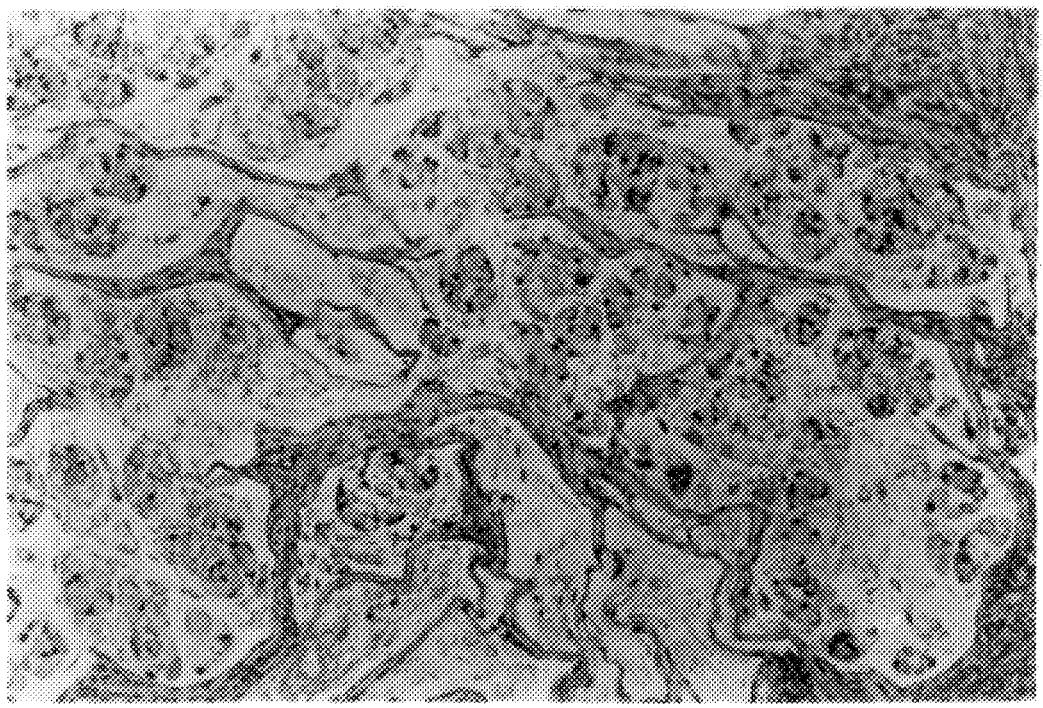
Figure 11:
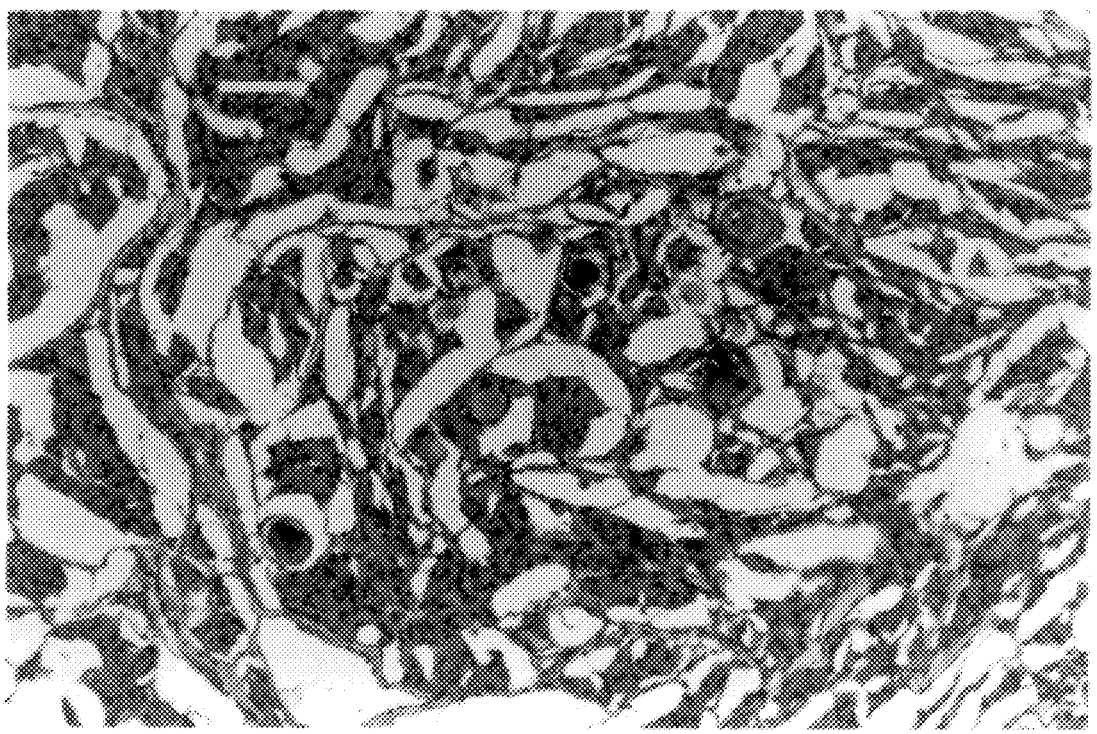
Figure 12:
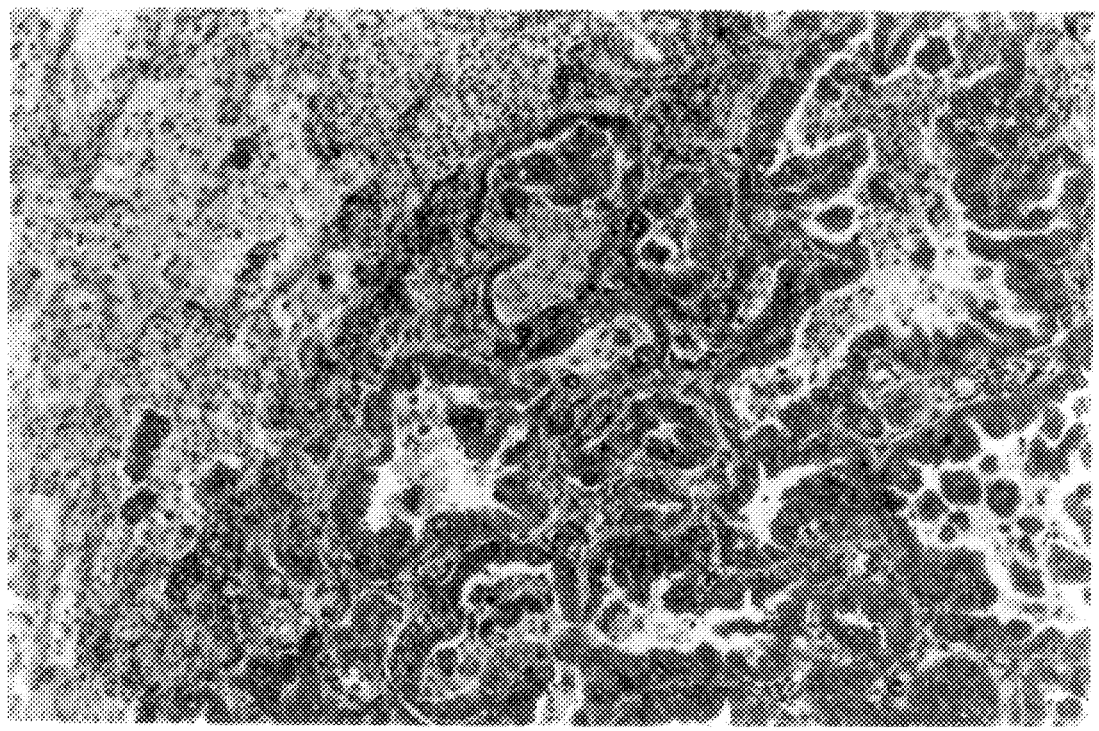
Figure 13:
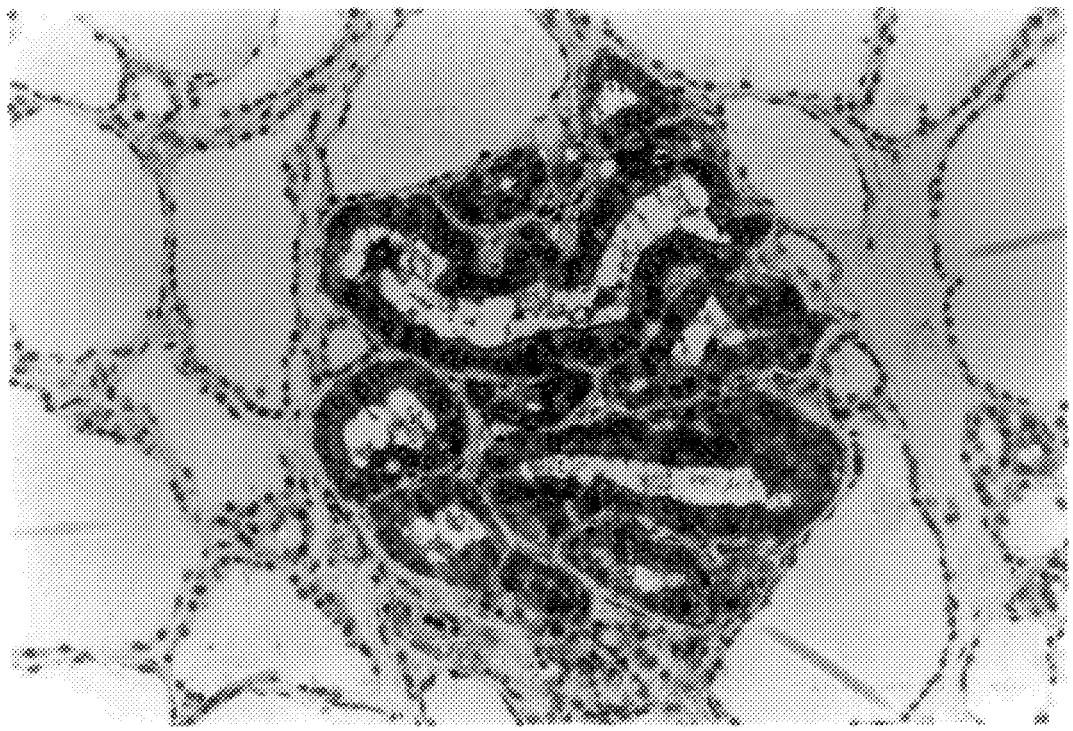
Figure 14:
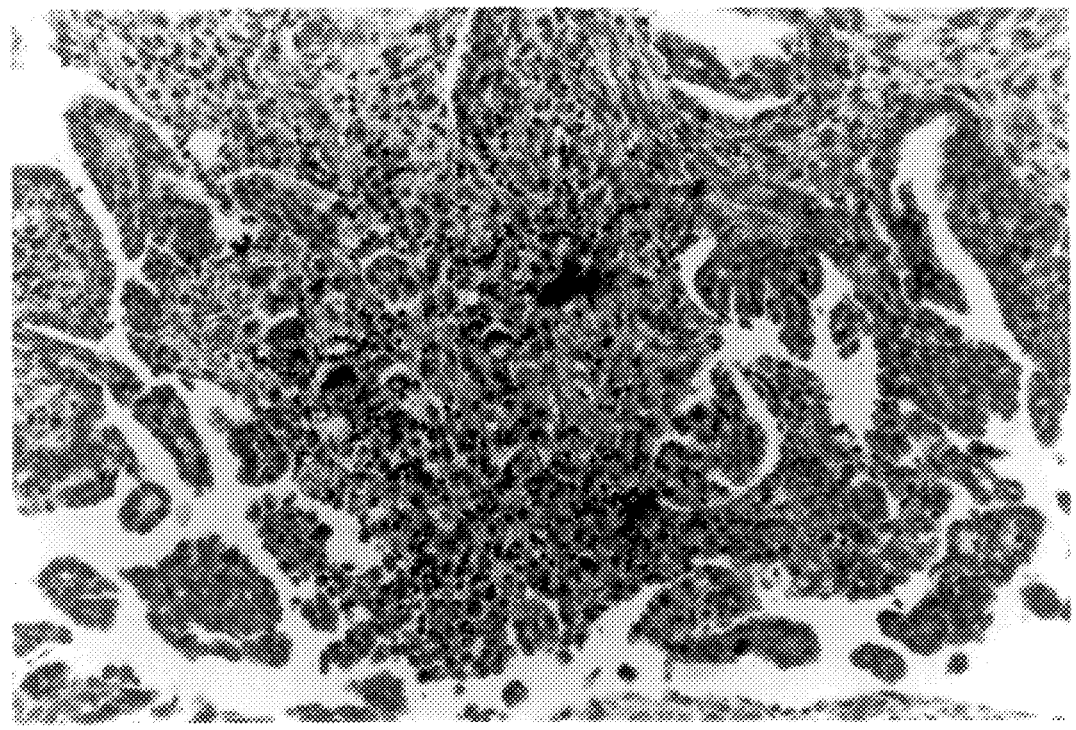
Figure 15:
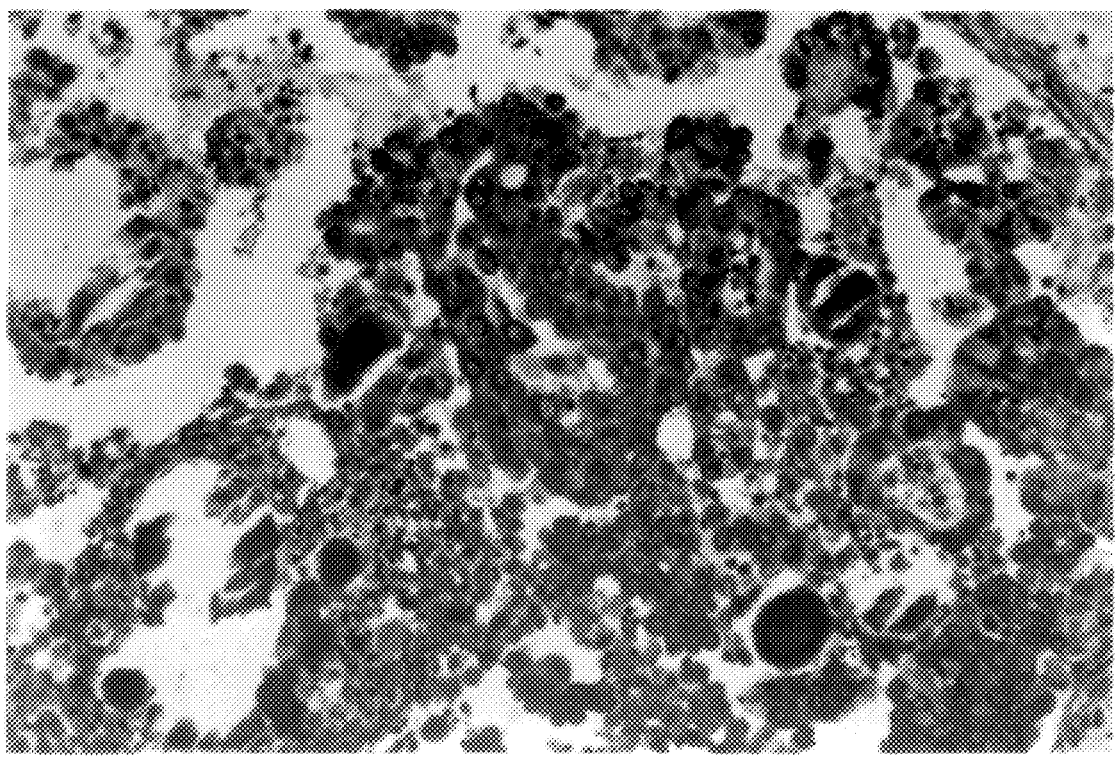
Figure 16:
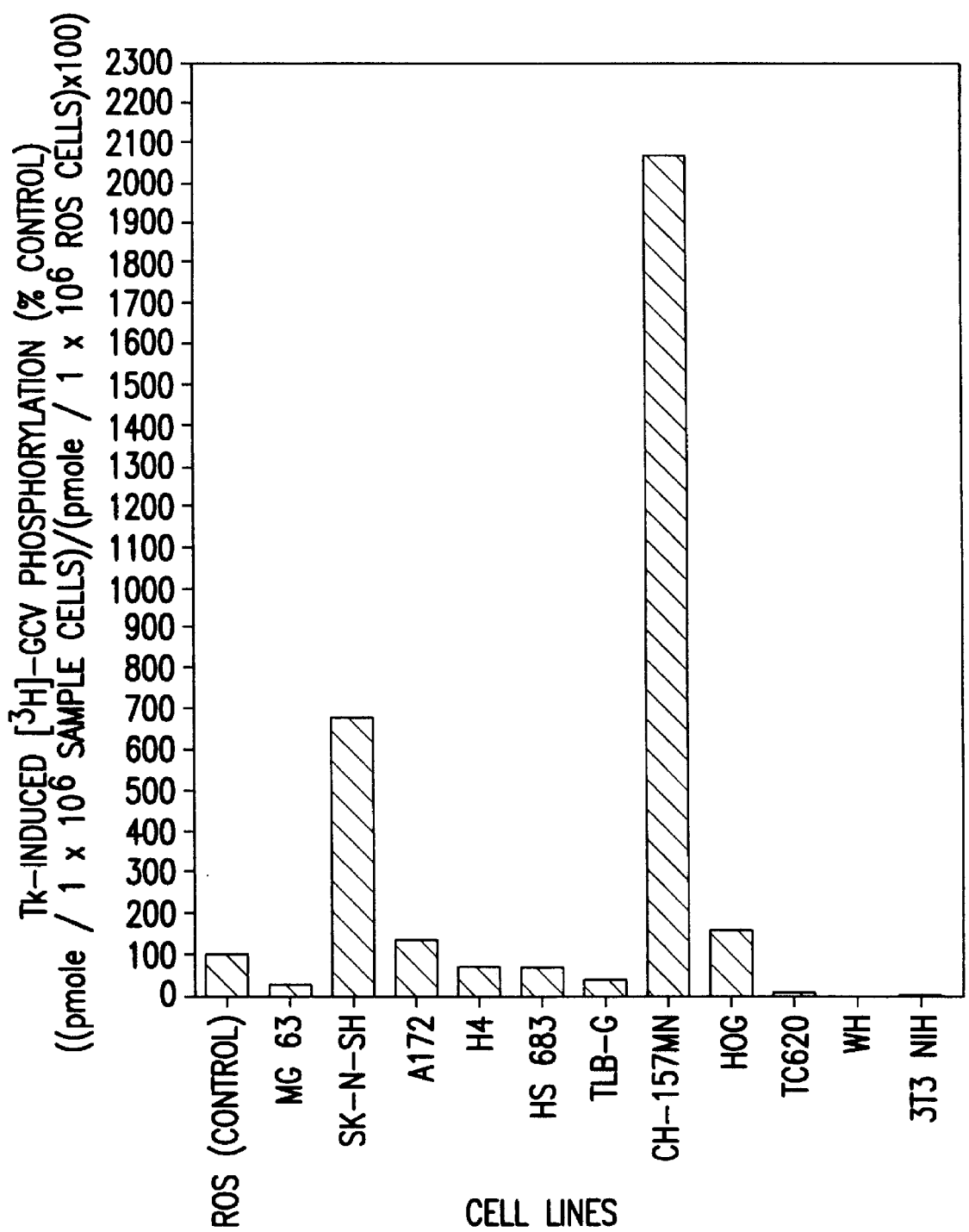

ROS sarcoma xenografts were induced by s.c. injection of ROS cells (1×10$^6$ cells/site) in athymic mice. After tumor formation, animals were treated with either ACV alone, Ad-OC-TK alone, or Ad-OC-TK plus daily ACV i.p. injection. After completion of a 7-day course of ACV, the AdOC-TK plus ACV treated group demonstrated no ROS tumor growth for up to 8 days and a significantly decreased growth rate for up to 20 days. (FIG. 4). After 1 month, the normal growth rate of ROS tumor resumed, and the experiment was terminated, Ad-OC-TK infection or ACV treatment alone did not affect the rate of tumor growth.

Development of Therapeutic Toxic Gene Therapy in Experimental Models of Human Prostate Cancer Bone Metastasis: Osteocalcin Promoted-based Toxic Gene Therapy.

Ad-OC-TK adenoviral vector was constructed as described above and the replication defective viruses were produced. A monolayer of a number of human cell lines were exposed to Ad-OC-TK, and TK activity and acyclovir-induced cell-kill were determined Ad-OC-TK anti-tumor activity was also tested in vivo by intratumor injection (subcutaneously) or intraosseous injection to previously established prostate tumors grown in the long bone. Therapeutic responses to tumors were determined by tumor size, histomorphology, apoptosis, and/or serum PSA (for LNCaP sublines C4-2 and C4-2 B induced tumors).

Ad-OC-TK expressed in both osteoblast-lineage cell types (ROS, MG63, MS), androgen-sensitive (LNCaP), and androgen-insensitive (C4-2, C4-2 B, DU-145, and PC-3) human cancer epithelial cell lines. Ad-OC-TK infection followed by acyclovir supplementation effectively eliminated the growth of osteoblast and non-osteoblast lineage tumor cell growth both in vitro and in vivo subcutaneously. Moreover, the growth of prostate tumors at the bone marrow space was notably eliminated, based upon histomorphologic X-ray and bone scan observation, at the end of a 30 day treatment period.

Vitamin $D_3$-Enhanced Osteocalcin Promoter-based Suicide Gene Therapy.

An adenoviral vector (Ad-OC-TK) consisting of OC promoter-suicide gene, thymidine kinase (TK), was constructed. This vector was found to be highly infectious against an array of prostate cancer and bone stromal cell lines. To enhance OC promoter activity, vitamin $D_3$ and its analogs were tested.

Ad-OC-TK activity was found to be expressed by a variety of human cancer cell lines, including osteosarcoma, prostate, melanoma, and breast; Ad-OC-TK, however, was not expressed by a human bladder transitional cell carcinoma cell line, WH, and NIH-3T3 cells. Intracellular TK activity was found to correlate well with acyclovir-induced cell-kill both in vitro and in vivo. Vitamin $D_3$ analogs may be employed as powerful modulators for OC promoter-mediated therapeutic gene expression.

What is claimed as new and is desired to be secured by Letters Patent of the United States is:

1. A therapeutic agent, comprising a recombinant adenovirus (Ad) vector containing an osteocalin (OC) promoter for expression of toxic thymidine (TK) kinase Ad-OC-TK.

2. The therapeutic agent of claim 1, further containing acyclovir (ACV).

3. The therapeutic agent of claim 1, further containing Vitamin $D_3$.

4. A method for treating a tumor, comprising delivering directly to said tumor a therapeutic agent, said therapeutic agent comprising (a) a recombinant adenovirus (Ad) vector containing an osteocalcin (OC) promoter driven toxic thymidine kinase, Ad-OC-TK optionally acyclovir (ACV).

5. The method of claim 4, wherein said tumor is osteosarcoma, breast cancer, prostate cancer, melanoma or brain tumor.

6. A method for treating a tumor as in claim 4, which further comprises delivering acyclovir (ACV) to said tumor.

* * * * *